United States Patent [19]

Baker et al.

[11] Patent Number: 5,157,043
[45] Date of Patent: * Oct. 20, 1992

[54] FUNGICIDAL N-PYRIDYL IMIDES

[75] Inventors: Don R. Baker; Charles Kezerian, both of Orinda; Francis H. Walker, Mill Valley; Keith H. Brownell, San Jose, all of Calif.

[73] Assignee: Imperial Chemical Industries PLC, London, Great Britain

[*] Notice: The portion of the term of this patent subsequent to Apr. 3, 2007 has been disclaimed.

[21] Appl. No.: 593,598

[22] Filed: Nov. 1, 1990

Related U.S. Application Data

[63] Continuation of Ser. No. 250,214, Sep. 29, 1988, abandoned.

[51] Int. Cl.$^5$ ............... A01N 43/40; C07D 213/75; C07D 213/76
[52] U.S. Cl. ............................. 514/346; 514/352; 546/292; 546/305; 546/309
[58] Field of Search ............ 546/261, 262, 292, 309; 514/332, 335, 346, 352

[56] References Cited

U.S. PATENT DOCUMENTS

| | | | |
|---|---|---|---|
| 4,767,772 | 8/1988 | Baker et al. | 514/346 |
| 4,831,044 | 5/1989 | Baker et al. | 514/349 |
| 4,914,115 | 4/1990 | Baker et al. | 514/346 |

Primary Examiner—Alan L. Rotman
Attorney, Agent, or Firm—Michael J. Bradley

[57] ABSTRACT

Novel fungicidal pyridyl carboximides having the general structural formula

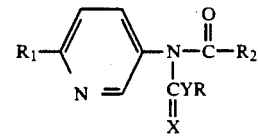

wherein
R is $C_1$–$C_6$ alkyl, preferably methyl;
$R_1$ is selected from the group consisting of halogen such as chlorine, fluorine and bromine, $C_1$–$C_3$ alkoxy such as propoxyethoxy and methoxy, preferably methoxy, and $C_2$–$C_4$ alkenyloxy;
$R_2$ is selected from the group consisting of hydrogen, $C_1$–$C_6$ alkyl, $C_4$–$C_6$ cycloalkyl, heterocyclic moieties, aryl, preferably phenyl, substituted aryl, preferably substituted phenyl wherein the substitutions are chlorine, fluorine, bromine, trifluoromethyl and $-NO_3$;
X is $-O$ or $-S$; and
Y is $-O$ or $-S$;

and fungicidally acceptable organic and inorganic salts thereof which are highly effective fungicides for use both as preventive and curative fungicides are disclosed herein.

11 Claims, No Drawings

FUNGICIDAL N-PYRIDYL IMIDES

This is a continuation of application Ser. No. 07/250,214, filed Sep. 29, 1988, now abandoned.

BACKGROUND OF THE INVENTION

Fungal infection of crops such as barley, rice, tomatoes, wheat, beans, roses, grapes and other agriculturally important crops can cause heavy losses in both quantity and quality of agricultural products. It is therefore extremely desirable to have means of preventing, controlling or eliminating fungal growth. Much preventive spraying with commercial fungicides is conducted to attempt to prevent the establishment and growth of fungi on agriculturally important crops. It would also be desirable to have a curative fungicide which, on detection of fungal infection, could control the fungi and eliminate the deleterious effects by use of a postinfection curative spray.

SUMMARY OF THE INVENTION

Novel fungicidal N-pyridyl imides having the formula

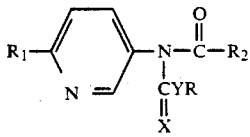

wherein
R is $C_1-C_6$ alkyl, preferably methyl;
$R_1$ is selected from the group consisting of halogen such as chlorine, fluorine and bromine, $C_1-C_3$ alkoxy such as propoxy, ethoxy and methoxy, preferably methoxy, and $C_2-C_4$ alkenyloxy;
$R_2$ is selected from the group consisting of hydrogen, $C_1-C_6$ alkyl, $C_4-C_6$ cycloalkyl, heterocyclic moieties, aryl, preferably phenyl, substituted aryl, preferably substituted phenyl wherein the substitutions are chlorine, fluorine, bromine, trifluoromethyl and $-NO_3$;
X is $-O$ or $-S$; and
Y is $-O$ or $-S$;
and fungicidally acceptable organic and inorganic salts thereof which are highly effective fungicides for use both as preventive and curative fungicides are disclosed herein.

The term "fungicide" is used to mean a compound which controls fungal growth. "Controls" includes prevention, destruction and inhibition of fungal growth. The term "curative" is meant to refer to a post-infection application of a fungicide which establishes control of fungal infection and prevents development of deleterious effects of the fungi on the host crop.

DETAILED DESCRIPTION

The novel fungicidal compounds of this invention are N-pyridyl imides having the general formula

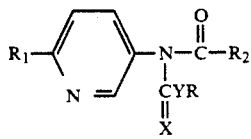

wherein
R is $C_1-C_6$ alkyl, preferably methyl;
$R_1$ is selected from the group consisting of halogen such as chlorine, fluorine and bromine, $C_1-C_3$ alkoxy such as propoxy, ethoxy and methoxy, preferably methoxy, and $C_2-C_4$ alkenyloxy;
$R_2$ is selected from the group consisting of hydrogen, $C_1-C_6$ alkyl, $C_4-C_6$ cycloalkyl, heterocyclic moieties, aryl, preferably phenyl, substituted aryl, preferably substituted phenyl wherein the substitutions are chlorine, fluorine, bromine, trifluoromethyl and $-NO_3$;
X is $-O$ or $-S$; and
Y is $-O$ or $-S$;
and fungicidally acceptable organic and inorganic salts thereof which are highly effective fungicides for use both as preventive and curative fungicides are disclosed herein.

The compounds of this invention can be generally prepared by a multi-step reaction process. The first step comprises reacting an appropriate aminopyridine with the appropriate acid chloride in an inert solvent such as dichloromethane in a suitable reactor such as a glass reaction flask. It is desirable to maintain an acid scavenger such as pyridine in the reaction vessel. The reaction generally will proceed at room temperature but will operate at a temperature range from $-30°$ to $80°$ C. The reaction should go to completion within 1 to 3 hours. The resulting intermediate product is recovered in a conventional manner by washing with an alkali solution such as sodium hydroxide and water, drying over conventional drying agents such as magnesium sulfate and crystallizing in hexane. The resulting carboxamide is then reacted with a properly substituted acid chloride in the presence of sodium hydride or other strong base in an inert solvent such as tetrahydrofuran (THF). An alternate procedure is to react the carboxamide or carbamate with a trialkylsilyl halide wherein the alkyl groups are $C_1-C_6$ alkyl in the presence of an acid scavenger such as triethylamine to silylate the amide, followed by reaction with a properly substituted acid chloride or chloroformate.

Salts of the various pyridyl imides can be conventionally prepared by reacting at least a molar amount of a Lewis acid with the carboxamide. Preferably the reaction is run in a solvent for the carboxamide. The prepared salt is recovered from the reaction mixture by conventional techniques.

Pyridyl carboxamides of the invention are basic. The unprotonated nitrogen atom of the pyridyl ring can be protonated by an acid, either organic or inorganic. Representative inorganic acids are hydrochloric, nitric, hydrobromic, sulfuric, sulfamic and phosphoric. Representative organic acids are acetic, trifluoroacetic, benzoic, benzenesulfonic, p-toluenesulfonic, naphthalenesulfonic, phenylphosphonic and organophosphonic. The salts so formed are also fungicidal.

EXAMPLE 1

Preparation of N-(2-Methoxy-5-pyridyl)formamide

5-Amino-2-methoxy pyridine (25 g, 0.2 mol) was added to ethylformate (50 ml). This solution was refluxed for eight hours. The volatiles were removed on a rotary evaporator at $30°$ C. and at aspirator vacuum. The resultant product was pink solid, 30.2 g, 99% of theory, m.p. $81°-83°$ C. The structure was confirmed by mass spectroscopy (MS), infrared (IR) and nuclear magnetic resonance (NMR) spectroscopy.

EXAMPLE 2

N-(2-Methoxy-5-pyridyl) N-formyltrimethylsilaneamine

N-(2-Methoxy-5-pyridyl)formamide (30.4 g, 0.2 mol) was added to 200 ml benzene. This was stirred with a mechanical stirrer under argon at 10° C. Trimethylsilyl chloride (25 g, 0.23 mol) was added. While stirring at 10° C., triethylamine (21 g, 0.21 mol) dissolved in 50 ml benzene was added dropwise over 0.5 hour. The slurry was warmed to room temperature and after 0.5 hour filtered. The salt cake was washed with 100 ml benzene and the combined filtrates concentrated on a rotary evaporator at 30° C. under aspirator vacuum. The dark liquid product was distilled under reduced pressure. A clear liquid, 39 g, 87% yield, (b.p. 87° C./0.25 mmHg). The product was stored under argon.

EXAMPLE 3

Preparation of S-Methyl-N-formyl-N-(2-methoxy-5-pyridyl) thiolcarbamate

N-(2-Methoxy-5-pyridyl)-N-formyl-trimethylsilane amide (2.28 g, 0.01 mol) was added to methylene chloride (25 ml) containing methyl chlorothiolformate (1.25 g, 0.011 mol). This solution was allowed to stand at room temperature overnight. This was then evaporated in vacuo and the residue purged with dry nitrogen at 50° C. for several hours. This gave 1.8 g of white solid as the title compound, m.p. 74°–77° C. The structure was confirmed by mass spectroscopy and its infra-red and nuclear magnetic resonance spectra.

Representative compounds of this invention and their properties are shown in Table I.

TABLE I

Structure:

$R_1$—pyridyl—N(—C(=O)—$R_2$)(—C(=X)YR)

| Cmpd. No. | R | $R_1$ | $R_2$ | X | Y | $n_D^{30}$ or melting point °C. |
|---|---|---|---|---|---|---|
| 1 | $CH_3$ | $-OCH_3$ | $-H$ | $-O$ | $-S$ | 74.0–77.0° C. |
| 2 | $CH_3$ | $-OCH_3$ | $-H$ | $-O$ | $-O$ | 1.5292 |
| 3 | $-n-C_4H_7$ | $-OCH_3$ | $-H$ | $-O$ | $-O$ | 1.5646 |
| 4 | $-C_2H_5$ | $-OCH_3$ | $-H$ | $-O$ | $-S$ | 83.0–85.0° C. |
| 5 | $-CH_3$ | $-OCH_3$ | $-CH_3$ | $-O$ | $-O$ | 60.0–63.0° C. |
| 6 | $-CH_3$ | $-OCH_3$ | $-CH_3$ | $-O$ | $-S$ | semi-solid |

EXAMPLE 4

Preventative Spray Evaluation Procedures

Barley Powdery Mildew (PM)

Northrup King Sunbar 401 barley seed is planted (12 seeds/2" pot) in a sandy-loam soil seven days prior to testing. The test compound is diluted in a 50/50 acetone/water solution to produce concentrations decreasing from 2250 ug/ml. Twelve ml of test solution are sprayed onto the barley plants with atomizing sprayers.

Twenty-four hours later, test plants are placed in an inoculation box equipped with a circulating fan. Barley plants with heavily sporulating *Erysiphe graminis* lesions are placed in front of the fan to dislodge and distribute the spores. After two minutes the fan is shut off and the chamber is left closed five minutes for the spores to settle. Inoculated plants are then placed on an automatic sub-irrigation greenhouse bench.

Results are recorded seven days following inoculation as percent disease control based on the percent reduction in infected area as compared to the untreated control plants. Compound concentrations which provide 90% disease control (EC 90) are determined from dosage/dilution curves.

Botrytis Bud Blight (BB)

Two white rose petals are placed in a petri dish lined with wet filter paper. The compound to be tested is diluted with a 50/50 acetone/water solution to produce concentrations decreasing from 2250 ug/ml. One-half ml of test solution is atomized onto the petals, and allowed to dry.

Inoculum is prepared by adding a 5 mm plug from a two-week old *Botrytis cinerea* culture grown on Elliot's V-8 agar, to 10 ml sterile distilled water plus 0.5 ml grape juice. A 20 ul drop of this inoculum suspension is placed on each petal. Petri dishes with inoculated petals are stored in sealed plastic boxes to maintain saturated humidity.

Results are read four days following inoculation as a percent reduction in necrotic area compared to the acetone/water controls. Compound concentrations which provide 90% disease control (EC 90) are determined from dosage/dilution curves.

The results are presented in Table II as an approximate EC 90 in parts per million. The entry (*) indicates no control at 750 ppm. 2250 ug/ml is equal to 2250 ppm. The entry (750) indicates partial control at 750 ppm. The entry (2250) indicates partial control at 2250 ppm. Only selected compounds were tested at 2250 ppm.

TABLE II

| Cmpd. No. | PM | BB |
|---|---|---|
| 1 | * | 250 |
| 2 | * | 25 |
| 3 | 2250 | (2250) |
| 4 | (2250) | 2250 |
| 5 | (750) | 250 |
| 6 | * | 25 |

The compounds of this invention are particularly effective against Botrytis bud blight and are particularly effective as preventative foliar sprays and curative foliar sprays when compared to standard commercial compounds used as Botrytis preventative and curative sprays. The compounds of the present invention are also particularly effective against *Erysiphe graminis*.

The compounds of the present invention are useful as fungicides, especially as preventative or curative fungicides, and can be applied in a variety of ways at various concentrations. In general, these compounds and formulations of these compounds can be applied directly to the crop foliage, the soil in which the crop is growing or in the irrigation water for the crop or soil. In practice, the compounds herein defined are formulated into fungicidal compositions, by admixture, in fungicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active fungicidal compounds may be formulated as wettable powders, as emulsifiable concentrates, as powdery dusts, as dusts, as solutions or as any of several other known types of formulations, depending upon the desired mode of application. Preferred formulations for preventative or curative fungicidal applications are wettable powders and emulsifiable concentrates. These formulations may contain as little as about 0.1% to as much as about 95% or more by weight of active ingredient. A fungicidally effective amount depends upon the nature of the seeds or plants to be treated and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the soil or plants either as a dry dust or as a dispersion in water or other liquid. Typical carriers for wettable powders include Fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Dry flowables or water dispersible granules are agglomerated wettable powders made by either pan granulation or by fluidized bed. The dry flowable is ultimately applied to the soil or plants as a dispersion in water or other liquid. These granules are dust-free and free flowing when dry and yet upon dilution in water, form homogeneous dispersions. Typical carriers for dry flowables include fuller's earth, kaolin clays, silicas and other readily wet organic or inorganic diluents. The dry flowables normally are prepared to contain from about 5% to about 95% of the active ingredient and usually contain a small amount of wetting, dispersing or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphtha, isophorone and other non-volatile organic solvents. For fungicidal application, these concentrates are dispersed in water or other liquid carrier and normally applied as a spray to the area to be treated. The percentage by weight of the essential active ingredient may vary according to the manner in which the composition is to be applied, but in general comprises about 0.1% to 95% of active ingredient by weight of the fungicidal composition.

Typical wetting, dispersing or emulsifying agents used in agricultural formulations include, for example, the alkyl and alkylaryl sulfonates and sulfates and their sodium salts; polyhydroxy alcohols; and other types of surface-active agents, many of which are available in commerce. The surface-active agent, when used, normally comprises from 0.1% to 15% by weight of the fungicidal composition.

Dusts, which are free-flowing admixtures of the active ingredient with finely divided solids such as talc, clays, flours and other organic and inorganic solids which act as dispersants and carriers for the toxicant, are useful formulations for many applications.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

| EXAMPLES OF TYPICAL FORMULATIONS | | | |
|---|---|---|---|
| Oil | | | |
| Ingredient | | | Weight % |
| Compound 1 | | | 1 |
| Oil solvent-heavy aromatic naphtha | | | 99 |
| Total | | | 100 |
| Emulsifiable Concentrate | | | |
| Compound 2 | | | 50 |
| Kerosene | | | 45 |
| Emulsifying agent (mixture of long chain ethoxylated polyethers with long chain sulfonate) | | | 5 |
| Total | | | 100 |
| Emulsifiable Concentrate | | | |
| Compound 3 | | | 90 |
| Kerosene | | | 5 |
| Emulsifying agent (mixture of long chain ethoxylated polyethers with long chain sulfonate) | | | 5 |
| Total | | | 100 |
| Dusts and/or Powders | | | |
| Ingredients | Wt. % | Wt. % | Wt. % |
| Compound 4 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

Other useful formulations for fungicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely divided form as a result of vaporization of a low boiling dispersant solvent carrier, such as the Freons, may also be used.

The fungicidal compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in low dosages.

We claim:

1. A compound having the structural formula

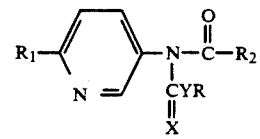

wherein

R is $C_1$ to $C_6$ alkyl;

$R_1$ is selected from the group consisting of halogen, $C_1$-$C_3$ alkoxy and $C_2$-$C_4$ alkenyloxy;

$R_2$ is selected from the group consisting of hydrogen, $C_1$-$C_6$ alkyl, $C_4$-$C_6$ cycloalkyl, phenyl and substituted phenyl, wherein said substituents are selected from the group consisting of chlorine, fluorine, bromine, trifluoromethyl and $-NO_3$;

X is $-O$ or $-S$; and

Y is $-O$ or $-S$;

or a fungicidally acceptable organic or inorganic salt thereof.

2. The compound of claim 1 wherein R is —CH$_3$, R$_1$ is —OCH$_3$, R$_2$ is —H, X is O and Y is —S.

3. The compound of claim 1 wherein R is —CH$_3$, R$_1$ is —OCH$_3$, R$_2$ is —H, X is O and Y is O.

4. The compound of claim 1 wherein R is —CH$_3$, R$_1$ is OCH$_3$, R$_2$ is —CH$_3$, X is O and Y is O.

5. The compound of claim 1 wherein R is —CH$_3$, R$_1$ is OCH$_3$, R$_2$ is —CH$_3$, X is O and Y is S.

6. A fungicidal composition comprising a fungicidally effective amount of a compound having the structural formula

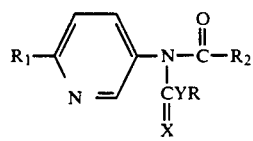

wherein
R is C$_1$ to C$_6$ alkyl;
R$_1$ is selected from the group consisting of halogen, C$_1$-C$_3$ alkoxy and C$_2$-C$_4$ alkenyloxy;
R$_2$ is selected from the group consisting of hydrogen, C$_1$-C$_6$ alkyl, C$_4$-C$_6$ cycloalkyl, phenyl and substituted phenyl, wherein said substituents are selected from the group consisting of chlorine, fluorine, bromine, trifluoromethyl and —NO$_3$;
X is —O or —S; and
Y is —O or —S;

or a fungicidally acceptable organic or inorganic salt thereof and an inert diluent carrier therefor.

7. The method of controlling fungi comprising applying to the area where control is desired a fungicidally effective amount of a compound having the formula

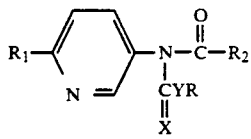

wherein
R is C$_1$ to C$_6$ alkyl;
R$_1$ is selected from the group consisting of halogen, C$_1$-C$_3$ alkoxy and C$_2$-C$_4$ alkenyloxy;
R$_2$ is selected from the group consisting of hydrogen, C$_1$-C$_6$ alkyl, C$_4$-C$_6$ cycloalkyl, phenyl and substituted phenyl, wherein said substituents are selected from the group consisting of chlorine, fluorine, bromine, trifluoromethyl and —NO$_3$;
X is —O or —S; and
Y is —O or —S;

or a fungicidally acceptable organic or inorganic salt thereof.

8. The method of claim 7 wherein R is —CH$_3$, R$_1$ is —OCH$_3$, R$_2$ is —H, X is O and Y is —S.

9. The method of claim 7 wherein R is —CH$_3$, R$_1$ is —OCH$_3$, R$_2$ is —H, X is O and Y is O.

10. The method of claim 7 wherein R is —CH$_3$, R$_1$ is OCH$_3$, R$_2$ is —CH$_3$, X is O and Y is O.

11. The method of claim 7 wherein R is —CH$_3$, R$_1$ is OCH$_3$, R$_2$ is —CH$_3$, X is O and Y is S.

* * * * *